(12) United States Patent
Haller et al.

(10) Patent No.: US 7,968,354 B1
(45) Date of Patent: Jun. 28, 2011

(54) METHODS FOR CORRELATING BACKSIDE AND FRONTSIDE DEFECTS DETECTED ON A SPECIMEN AND CLASSIFICATION OF BACKSIDE DEFECTS

(75) Inventors: Kurt Haller, Pleasanton, CA (US); Susan S. Lopez, Santa Clara, CA (US)

(73) Assignee: KLA-Tencor Technologies Corp., Milpitas, CA (US)

(*) Notice: Subject to any disclaimer, the term of this patent is extended or adjusted under 35 U.S.C. 154(b) by 1699 days.

(21) Appl. No.: 10/678,883

(22) Filed: Oct. 3, 2003

Related U.S. Application Data

(60) Provisional application No. 60/416,136, filed on Oct. 4, 2002.

(51) Int. Cl.
    *G01R 31/26* (2006.01)
(52) U.S. Cl. ............ 438/14; 438/16; 257/E21.521; 356/237.1; 356/237.2; 356/237.3; 356/237.5; 702/83; 382/145; 382/149
(58) Field of Classification Search ............ 438/5, 14, 438/692, 800, 16; 702/35, 155, 33, 40, 83; 382/145, 149; 356/237.1, 237.2, 237.3, 237.5
See application file for complete search history.

(56) References Cited

U.S. PATENT DOCUMENTS

| | | | |
|---|---|---|---|
| 4,556,317 A | 12/1985 | Sandland et al. | |
| 4,599,558 A | 7/1986 | Castellano, Jr. et al. | |
| 4,618,938 A | 10/1986 | Sandland et al. | |
| 5,208,648 A | 5/1993 | Batchelder et al. | |
| 5,220,403 A | 6/1993 | Batchelder et al. | |
| 5,563,702 A | 10/1996 | Emery et al. | |
| 5,644,393 A | 7/1997 | Nakamura et al. | |
| 5,991,699 A | 11/1999 | Kulkarni et al. | |
| 6,104,835 A | 8/2000 | Han | |
| 6,134,343 A * | 10/2000 | Nichani | 382/141 |
| 6,156,580 A * | 12/2000 | Wooten et al. | 438/16 |
| 6,233,719 B1 | 5/2001 | Hardikar et al. | |

(Continued)

FOREIGN PATENT DOCUMENTS

JP 62-39705 2/1987

(Continued)

OTHER PUBLICATIONS

Otsu, "A Threshold Selection Method from Gray-Level Histograms," IEEE Transactions on Systems, Man, and Cybernetics, vol. SMC-9, No. 1, Jan. 1979, pp. 62-66.

(Continued)

*Primary Examiner* — Hsien-ming Lee
(74) *Attorney, Agent, or Firm* — Ann Marie Mewherter

(57) ABSTRACT

Computer-implemented methods that include correlating a backside defect with a frontside defect detected on a specimen are provided. The defects are correlated if a portion of the backside defect on the backside of the specimen is opposite to a portion of the frontside defect on the frontside of the specimen. In particular, the defects are correlated if the portion of the backside defect is aligned with the portion of the frontside defect along an axis perpendicular to the frontside and the backside of the specimen. The method may also include altering a parameter of a process tool in response to the backside defect to reduce frontside defects on additional specimen processed in the process tool. Computer-implemented methods for analyzing data representing spatial characteristics of backside defects detected on a specimen to classify the backside defects are also provided. Analyzing the data may include spatial signature analysis of the data.

19 Claims, 3 Drawing Sheets

U.S. PATENT DOCUMENTS

| | | | |
|---|---|---|---|
| 6,401,008 B1 * | 6/2002 | Ehrichs et al. | 700/228 |
| 6,825,487 B2 * | 11/2004 | Preece | 250/559.4 |
| 6,829,559 B2 * | 12/2004 | Bultman et al. | 702/155 |
| 2002/0142617 A1 * | 10/2002 | Stanton | 438/749 |
| 2003/0139838 A1 | 7/2003 | Marella | |

FOREIGN PATENT DOCUMENTS

| | | |
|---|---|---|
| JP | 6-347415 | 12/1994 |
| JP | 6-349908 | 12/1994 |
| JP | 8-102479 | 4/1996 |
| WO | 99/22310 | 5/1999 |
| WO | 99/59200 | 11/1999 |
| WO | 00/03234 | 1/2000 |
| WO | 01/40145 | 6/2001 |

OTHER PUBLICATIONS

Cheema et al., "Wafer Back Side Inspection Applications for Yield Protection and Enhancement," presented at the Advanced Semiconductor Manufacturing Conference, Boston, MA, Apr. 30, 2002, 8 pages.

Diebold, *Handbook of Silicon Semiconductor Metrology*, © 2001 by Marcel Dekker, Inc., pp. 694-698.

* cited by examiner

METHODS FOR CORRELATING BACKSIDE AND FRONTSIDE DEFECTS DETECTED ON A SPECIMEN AND CLASSIFICATION OF BACKSIDE DEFECTS

PRIORITY CLAIM

This application claims priority to U.S. Provisional Application No. 60/416,136 entitled "Methods for Correlating Backside and Frontside Defects Detected on a Specimen and Classification of Backside Defects," filed Oct. 4, 2002.

BACKGROUND OF THE INVENTION

1. Field of the Invention

This invention generally relates to systems and methods for inspection of a specimen such as a semiconductor wafer. Certain embodiments relate to methods for correlating backside and frontside defects detected on a specimen and classification of backside defects.

2. Description of the Related Art

Fabricating semiconductor devices such as logic and memory devices includes processing a semiconductor wafer using a number of semiconductor fabrication processes to form various features and multiple levels of the semiconductor devices. For example, lithography is a semiconductor fabrication process which typically involves transferring a pattern to a resist arranged on a semiconductor wafer. Additional examples of semiconductor fabrication processes may include chemical-mechanical polishing, etch, deposition, and ion implantation. Multiple semiconductor devices may be fabricated in an arrangement on a semiconductor wafer and then separated into individual semiconductor devices.

During each semiconductor fabrication process, defects such as particulate contamination and pattern defects may be introduced into the semiconductor devices. Defects may be isolated in a single semiconductor device on a semiconductor wafer containing several hundred semiconductor devices. More commonly, the defects occur in many semiconductor devices formed across an entire semiconductor wafer. Different types of defects may result from different process or tool marginalities. For example, defects that are caused by un-optimized processes or tools, incompatibility of materials, up-optimized materials, and/or un-optimized characteristics of materials are commonly referred to as "systematic defects." Defects that occur unexpectedly or unpredictably over time, which may be caused by tool failure, variations in processing materials or chemicals, particles, contamination, and other environmental marginalities are often referred to as "random defects."

Successful fabrication of semiconductor devices is often limited by the presence of defects in the semiconductor devices. Monitoring semiconductor fabrication processes over time has become increasingly important in the industry to improve or maintain yield as the dimensions of semiconductor devices shrink. Macro-level defect inspection may be used to detect yield-limiting large scale defects on a wafer. Such defects may be commonly referred to as "macro defects" and are typically characterized as having a lateral dimension of greater than about 25 µm. Such large scale defects may include resist or developer problems such as lifting resist, thin resist, extra resist coverage, incomplete or missing resist, which may be caused by clogged dispense nozzles or an incorrect process sequence, and developer or water spots. Additional examples of defects may include regions of defocus that may be caused by particles on the backside of a wafer, reticle errors such as tilted reticles, out-of-focus exposure or incorrectly selected reticles, scratches, pattern integrity problems such as over or under developing of the resist, contamination such as particles or fibers, and non-uniform or incomplete edge bead removal ("EBR"). Other defects are commonly referred to as "hot spots," which generally refers to a resist exposure defect which may be caused, for example, by a depth of focus limitation of an exposure tool, an exposure tool malfunction, a non-planar surface of the semiconductor wafer at the time of exposure, foreign material on a backside of the semiconductor wafer or on a surface of a supporting device, or a design constraint.

Macro-level defect inspection may involve inspecting all of the product wafers in a lot or only a number of product wafers in each lot because such defects may be particularly deleterious to the yield of semiconductor manufacturing processes. In addition, the high cost associated with semiconductor device fabrication necessitates macro-level defect inspection such that the effects of yield-limiting large scale defects may be minimized. Macro-level defect inspection of product wafers typically includes only inspection on the frontside of the product wafers (i.e., the surface of the wafers on which the semiconductor devices are being formed). The surface of the product wafers on which semiconductor devices are not formed is commonly referred to as the "backside" of the wafers. Macro-level defect inspection is typically performed on the backside of non-product semiconductor wafers (i.e., un-patterned wafers or "monitor wafers"), which have been run through a process tool, to monitor the conditions of the process tool.

Micro-level defect inspection may be used to detect any defects having dimensions smaller than the dimensions of macro-level defects. Such inspection is typically performed with different tools than systems designed for macro-level defect inspection because of the different resolution requirements needed to detect the different sized defects. Micro-level defect inspection is typically used to inspect the frontside of semiconductor wafers. Micro-level defect inspection may also be used to detect defects on the frontside of patterned and unpatterned wafers. For example, micro-level defect inspection may be used to analyze a resist coating process or a resist develop process on a unpatterned wafer. Alternatively, micro-level defect inspection may be used to analyze an exposure tool and exposure process on a patterned wafer. Wafers for these two micro-level defect inspection may be performed with non-product wafers. In this manner, these non-product wafers may be reworked and reused multiple times, and abnormal process and/or tool deviations may be readily detected and corrected prior to manufacturing devices on product wafers. Micro-level defect inspection (in addition to, or as an alternative to macro-level defect inspection) may also be performed periodically on the frontside of product wafers to monitor drift in the process and/or the tool and to monitor the presence of random defects on the frontside of the product wafers.

SUMMARY OF THE INVENTION

Methods for process control and monitoring in the semiconductor industry currently rely primarily on frontside defect inspection of wafers. However, backside defect inspection is becoming more common in the semiconductor industry due to, at least in part, the recent advances in technology for inspecting the backside of wafers. Although these defects may be not be present on the frontside of the wafers, backside defects may contribute to defects on the frontside of the wafers. Backside defects may also contribute to defects on the frontside and/or backside of other wafers processed with or after a defective wafer. Therefore, the various embodiments described herein in which backside defect inspection results are used to analyze, monitor, and control a semiconductor fabrication process may be used to reduce the presence of defects in fabricated semiconductor devices thereby increasing the yield of a semiconductor fabrication process.

As the "process window" for semiconductor fabrication processes decreases in conjunction with reductions in the dimensions of semiconductor devices, the impact of backside defects on the yield of fabrication processes increases. For example, as the depth of focus of an exposure system used in a lithography step decreases, backside defects on a wafer may cause more localized regions on the wafer to be out-of-focus during the exposure than in the past. Therefore, the backside defects may cause more variations in the characteristics and/or dimensions of features in a patterned resist across the wafer. Although the contribution of the backside defects to these variations may have been negligible or undetectable in the past, the backside defect may have a significantly greater impact on these variations as the process window of semiconductor fabrication process continues to shrink.

Backside defects may also cause variations in characteristics and/or dimensions of features of other patterns formed on a wafer (i.e., patterns formed by etching a wafer). In addition, backside defects may cause missing features in a patterned resist and/or other patterns formed on a wafer, variations in characteristics of deposited or polished materials across a wafer (i.e., variations in the thickness of a deposited dielectric material or a polished dielectric material), variations in the characteristics of annealed materials across a wafer, and/or non-working semiconductor devices (i.e., due to micro-arcing in an etch process). Therefore, it is anticipated that the various embodiments described herein, which use backside defect inspection results to analyze, monitor, and control a semiconductor fabrication process, may be used to reduce variations in wafer uniformity thereby mitigating decreases in semiconductor device yield due to reduction in the process window.

Backside defects may also be more problematic for wafers that are polished on both the frontside and the backside. For example, the surface roughness of an unpolished backside of a wafer may allow relatively small defects such as small particles to be partially or entirely disposed within "pits" or "cavities" in the backside of the wafer. In this manner, relatively small backside defects may not contribute to wafer non-uniformities of single-sided polished wafers and, therefore, may have essentially no discernable effects on semiconductor fabrication yield. However, since double-side polished wafers will have a relatively smooth backside, even relatively small defects may contribute to wafer non-uniformities because the defects cannot "hide" within surface roughness on the backside of the wafer. Therefore, it is anticipated that the various embodiments described herein may be used to reduce variations in wafer uniformity thereby mitigating reduction in semiconductor device yield due to the use of double-sided polished wafers. The embodiments described herein may also have additional advantages as described herein.

An embodiment of the invention relates to a computer-implemented method that includes correlating a backside defect detected on a specimen with a frontside defect detected on the specimen. The backside and frontside defects may be correlated if a portion of the backside defect on a backside of the specimen is opposite to a portion of the frontside defect on a frontside of the specimen. In particular, if the portion of the backside defect is aligned with the portion of the frontside defect along an axis perpendicular to the frontside and the backside of the specimen, the backside and frontside defects may be correlated. The portion of the backside defect may include at least 5% of a cross-sectional area of the backside defect, parallel to the upper surface of the backside of the specimen. Similarly, the portion of the frontside defect may include at least 5% of a cross-sectional area of the frontside defect, parallel to the upper surface of the frontside of the specimen. The portions of the frontside and backside defects that must be opposite to one another in order to correlate the defects may vary, however, depending upon, for example, the types of defects detected on the different sides of the specimen. The specimen may include a semiconductor wafer, which is used interchangeably herein with the term "wafer." However, the specimen may include any other specimen known in the art such as a specimen that has more than one side on which defects may be detected.

In some embodiments, the method may include identifying data representative of a signature of a chuck of a process tool within data generated during detection of the backside defect. Such embodiments may also include removing the data representing the signature of the chuck from the data generated during detection of the backside defect prior to correlating the defects. In this manner, data generated during detection of the frontside defects may not be erroneously correlated with the data representing the signature of the chuck.

In one embodiment, the method may also include generating a single visual representation of the specimen. For example, the method may include generating visual representations of the frontside and the backside of the specimen. The visual representations may include images of the different sides of the specimen generated by one or more inspection systems. Alternatively, the visual representations may include graphical representations, such as two-dimensional maps, of the different sides of the specimen that illustrate characteristics of the specimen as a function of position on the specimen. The characteristics may be determined from data generated by one or more inspection systems used to detect defects on the front and backsides of the specimen.

Such embodiments may also include altering one of the visual representations such that the altered visual representation appears as a mirror image of its original visual representation. The method may further include superimposing the altered and the unaltered visual representations to generate an overall visual representation of the specimen. The single, overall visual representation of the specimen may illustrate the backside defect and the frontside defect with different formatting to visually differentiate the backside defect and the frontside defect. In additional embodiments, the method may include determining if a portion of the backside defect on the backside of the specimen is opposite to a portion of the frontside defect on the frontside of the specimen from the overall visual representation. In some embodiments, the overall visual representation may not illustrate additional backside defects detected on the specimen and additional frontside defect detected on the specimen if at least a portion of each of the additional backside defects is not opposite to a portion of one of the additional frontside defects.

In another embodiment, the method may include comparing coordinates defining a location of the backside defect with coordinates defining a location of the frontside defect to determine if a portion of the backside defect on the backside of the specimen is opposite to the portion of the frontside defect on the frontside of the specimen. In some embodiments, the method may include altering the coordinates defining the location of the backside defect or altering the coordinates defining the location of the frontside defect prior to comparing the coordinates. In this manner, the locations of the backside defect and the frontside defects may be defined as if the backside and frontside defects were detected on the same side of the specimen.

In additional embodiments, the method may include classifying the backside defect. In some such embodiments, the method may also include determining a root cause of the backside defect from data representing processing history of the specimen. In other such embodiments, the method may include determining parameters for classifying the frontside defect from the classification of the backside defect. For example, the number of possible classes that are considered for the frontside defect may be reduced based on the classification of the backside defect. For instance, if the backside defect is a particle, then the possibility that the frontside defect is a scratch may not be considered during classification of the frontside defect. Determining parameters for classification of the frontside defect may increase the accuracy of such classification and may increase the throughput of the defect analysis or review process. In further embodiments, the method may include determining a root cause of the frontside defect from the classification of the backside defect. In some embodiments, the method may include altering a parameter of a process tool in response to the classification of the backside defect. In additional embodiments, the method may include altering a parameter of a process tool in response to the backside defect to reduce occurrence of the frontside defect and/or the backside defect on additional specimen processed in the process tool. The method may also include other steps as described herein.

An additional embodiment relates to a computer-implemented method that includes correlating a backside defect detected on a backside of a specimen with a frontside defect detected on a frontside of the specimen if the backside defect and the frontside defect satisfy one or more proximity criteria. In one embodiment, the method may also include defining the backside defect as a geometrical figure having lateral dimensions larger than the backside defect. In such an embodiment, the one or more proximity criteria may be satisfied if at least a portion of the geometrical figure is opposite to at least a portion of the frontside defect. In addition or alternatively, the method may include defining the frontside defect as a geometrical figured having lateral dimensions larger than the frontside defect. In such embodiments, the one or more proximity criteria may be satisfied if at least a portion of the geometrical figure is opposite to at least a portion of the backside defect or a geometrical figure defining the backside defect. In some embodiments, the one or more proximity criteria may be satisfied if at least a portion of the backside defect is opposite to at least a portion of the frontside defect. This method may also include other steps as described herein.

Another embodiment relates to a computer-implemented method that includes analyzing data representing spatial characteristics of backside defects detected on a specimen to classify the backside defects. In one embodiment, analyzing the data may include spatial signature analysis of the data. In some embodiments, the method may include determining if data generated during detection of the backside defects is representative of a signature of a chuck of a process tool. This method may also include other steps as described herein.

Additional embodiments relate to a carrier medium that includes program instructions executable on a computer system. In one embodiment, the program instructions may be executable to correlate a backside defect detected on a specimen with a frontside defect detected on the specimen if a portion of the backside defect on a backside of the specimen is opposite to a portion of the frontside defect on a frontside of the specimen. In an additional embodiment, the program instructions may be executable to correlate a backside defect detected on a backside of a specimen with a frontside defect detected on a frontside of the specimen if the backside defect and the frontside defect satisfy one or more proximity criteria. In another embodiment, the program instructions may be executable to analyze data representing spatial characteristics of a backside defect detected on a specimen to thereby determine a classification of the backside defect. In each embodiment, the carrier medium may include additional program instructions as described herein.

BRIEF DESCRIPTION OF THE DRAWINGS

Other objects and advantages of the invention will become apparent upon reading the following detailed description and upon reference to the accompanying drawings in which.

Figure 1A:
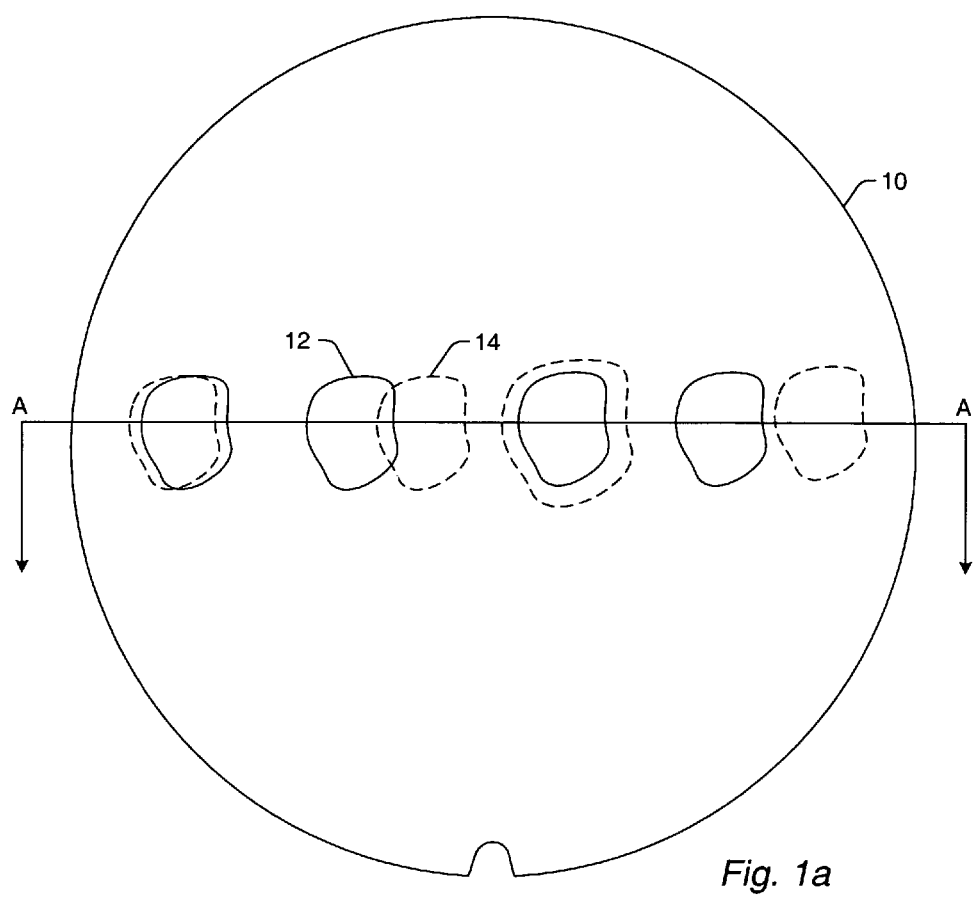
FIG. 1a is a top view of a wafer and several frontside and backside defects that were detected on the wafer.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

The following description generally relates to computer-implemented methods for analyzing backside defect inspection results and for reducing the deleterious effects of backside defects on semiconductor fabrication processes. For example, backside defects such as "fall-on particles," which may shed from the backside of post-processed wafer and may land on a wafer below, "sticky particles," which may migrate onto another wafer if the other wafer physically contacts the backside of the wafer, and "residue" may cause yield loss, reduced throughput, and increased scrap. It is estimated that backside defects may contribute to about 1% to about 10% or more of the yield losses of semiconductor device manufacturing. Yield losses caused by backside defects are also expected to increase as design groundrules shrink and as double-sided polish wafers are becoming increasingly used to manufacture semiconductor devices. For example, as the groundrules approach 100 nm production, optimal wafer uniformity becomes an increasingly important issue in lithography processing due to the tightening depth of focus requirements of lithography and the use of double-sided polish wafers. In addition, for 300 mm semiconductor device manufacturing, controlling wafer uniformity over the much larger area is more difficult than in manufacturing of 200 mm wafers.

The computer-implemented methods described herein may be used to improve the yield of semiconductor manufacturing processes, to increase throughput, and to reduce scrap and production costs. For example, if backside defects may be reduced, production costs may decrease through the elimination of one or more clean steps and through the reduction in maintenance and part replacement. In addition, the methods described herein may be used in a number of applications such as process tool qualification, process tool monitoring using product and/or non-product wafers, process development, and process sequence improvements.

As used herein, the term "defect" generally refers to a macro-level defect including any of the macro-level defects described above or a micro-level defect. A defect may be generally defined as an abnormality formed on or within a specimen that may adversely affect the performance or functionality of a device formed on the specimen (i.e., reduce a characteristic such as speed or cause a device failure that may or may not cause a device to be non-working) or additional devices formed on the specimen if the cause is not fixed.

Defects may be caused by individual process marginalities. Defects may also be caused by process integration marginalities or interactions between multiple processes. For example, a defect may be contamination on a specimen, abnormal structures on the specimen, or damage to the specimen. Contamination may include, but is not limited to, particles, fibers, or residual material remaining on a specimen after a process step. Contamination may also include organic or inorganic material such as a resist, a dielectric material, and/or a conductive material. Abnormal structures on a specimen may include, but are not limited to, missing structures, bridging structures, voids formed within structures, structures that have a lateral dimension that is larger than or smaller than a predetermined range of values, and/or structures having an abnormal profile such as roughness, fluting, rounding, and/or a sidewall angle that is larger than or smaller than a predetermined range of values. Damage to the specimen may include, for example, a surface scratch, roughness, breakage of the specimen, or breakage of structures formed on the specimen. As used herein, the term "structures" generally refers to an unpatterned layer of material formed on a specimen, patterned features formed on a specimen, or any combination thereof.

A defect may be present in any location on a specimen. In addition, any number of each of the defects may also be present on the specimen. The term "frontside defect" is used herein to refer to a defect located on one side of the specimen, and the term "backside defect" is used herein to refer to a defect located on another, opposing side of the specimen. In the case of a semiconductor wafer, or a "wafer," a frontside defect is located on an upper side, or "frontside," of the wafer (i.e., the surface of the wafer upon which semiconductor devices will be or have been formed), and a backside defect is located on a lower surface, or "backside," of the wafer (i.e., the surface of the wafer upon which semiconductor devices will not be formed). Although the frontside of a wafer is usually polished, the backside of a wafer may be unpolished (i.e., a single-sided polish wafer) or polished (i.e., a double-sided polish wafer). Any number of frontside defects and backside defects may be present on the frontside and backside of a specimen, respectively.

The term "wafer" generally refers to substrates formed of a semiconductor or a non-semiconductor material. Examples of such a semiconductor or a non-semiconductor material include, but are not limited to, monocrystalline silicon, gallium arsenide, and indium phosphide. Such substrates may be commonly found and/or processed in semiconductor fabrication facilities.

A wafer may include only the substrate such as a virgin wafer or a wafer prior to a first-pass lithography process. Alternatively, a wafer may include one or more layers that may be formed upon a semiconductor substrate. For example, such layers may include, but are not limited to, a resist, a dielectric material, and a conductive material. A resist includes any material that may be patterned by an optical lithography technique, an e-beam lithography technique, or an X-ray lithography technique. Examples of a dielectric material include, but are not limited to, silicon dioxide, silicon nitride, silicon oxynitride, and titanium nitride. Additional examples of a dielectric material include "low-k" dielectric materials such as Black Diamond™ which is commercially available from Applied Materials, Inc., Santa Clara, Calif., CORAL™ commercially available from Novellus Systems, Inc., San Jose, Calif., "ultra-low k" dielectric materials such as "zero gels," and "high-k" dielectric materials such as tantalum pentoxide. In addition, examples of a conductive material may include, but are not limited to, aluminum, polysilicon, and copper.

One or more layers formed on a wafer may be patterned or unpatterned. For example, a wafer may include a plurality of dies having repeatable pattern features. Formation and processing of such layers of material may ultimately result in completed semiconductor devices. As such, a wafer may include a substrate on which not all layers of a complete semiconductor device have been formed or a substrate on which all layers of a complete semiconductor device have been formed.

The specimen may further include at least a portion of a thin-film head die formed on a wafer, at least a portion of a micro-electro-mechanical system (MEMS) device formed on a wafer, and at least a portion of other components that may include photonics and optoelectronic devices such as lasers, waveguides and other passive components processed on wafers, print heads, and bio-chip devices processed on wafers.

In some cases, the specimen may include a reticle. A "reticle," or a "mask," is generally defined as a substantially transparent substrate having substantially opaque regions formed thereon and configured in a pattern. The substrate may include, for example, a glass material such as quartz. A reticle may be disposed above a resist-covered wafer during an exposure step of a lithography process such that the pattern on the reticle may be transferred to the resist. For example, substantially opaque regions of the reticle may protect underlying regions of the resist from exposure to an energy source.

In one embodiment, a computer-implemented method includes correlating a backside defect detected on a specimen with a frontside defect detected on the specimen. Although in further description of this embodiment, the term "specimen" is used interchangeably with the term "wafer," it is to be understood that this embodiment and all other embodiments described herein are not limited to wafers and can be performed for any of the other specimens described above. The backside and frontside defects may be detected on the specimen by inspecting the backside and the frontside of the specimen with the same or different inspection systems. Inspecting the backside and the frontside of the specimen may include macro-level defect inspection and/or micro-level defect inspection. Alternatively, the frontside defects may be detected on the specimen by metrology. The metrology performed on the frontside of the specimen may be include any metrology technique known in the art. The different inspection systems may be of the same or different make and model. One inspection system that may be used to inspect both sides of a specimen is the SP1 laser-based wafer inspection tool commercially available from KLA-Tencor, San Jose, Calif., which includes a Back Side Inspection Module (BSIM). The SP1 BSIM module can be used to detect defects on both polished and unpolished backsides of wafers.

The BSIM enables non-destructive frontside and backside inspection of a specimen such as a wafer through wafer edge handling and a "flipping" mechanism. Therefore, the wafer handling is designed such that the frontside of the wafer is not damaged during inspection of the backside of the wafer. In this manner, backside inspection of both product and non-product wafers may be performed using the SP1. Being able to inspect both sides of a product wafer advantageously provides the ability to correlate backside defects with product yield data, to gather frontside and backside defect data on a single wafer (as opposed to comparing frontside defects on a product wafer to backside defects on a non-product wafer), and to reuse non-product wafers since the frontside of these wafers are also not damaged during backside inspection as in other systems and methods that may be used for backside inspection. For example, other systems and methods typically involve loading a non-product wafer frontside down in an inspection system and scanning the backside of the wafer to detect backside defects on the wafer. In addition, being able to inspect both sides of a wafer with a single, non-destructive system may simplify methods for correlating defects on different sides of the wafer with each other. However, as is illustrated herein, it is not necessary that backside and frontside inspection are performed using a single system in order to correlate defects on different sides of the wafer. Other examples of inspection systems that may be used to detect defects on at least one side of a specimen include the KLA-Tencor 6000 series laser based inspection tools and the KLA-Tencor Viper 2430 system.

Backside inspection may be performed at various points in a semiconductor fabrication process. For example, incoming product wafers may be inspected for backside defects for quality control of the incoming product wafers. Wafers may also be inspected for backside defects after thin film deposition to monitor micro-arcing damage of the thin films and/or wafer, prior to lithography to monitor backside defects that may cause frontside out-of-focus defects or frontside hot spot defects, prior to ion implantation to monitor backside residual resist defects, prior to a pre-gate cleaning of product wafers to evaluate the cleaning process, after a cleaning step to monitor backside copper defects resulting from etch and remaining after cleaning, after etch to monitor backside defects caused by micro-arcing damage of thin films or structures and/or a wafer, after etch to monitor backside residue defects such as copper, and after chemical-mechanical polishing (CMP) to monitor backside slurry defects. Backside inspection may also be performed at various times for process and/or tool development or qualification. For example, backside inspection maybe performed to monitor a "fingerprint," or spatial signature, of a chuck or wafer handler of a process tool, to reduce backside contamination caused by parameters or components of the process tool itself, and to optimize backside cleaning steps such as after CMP to reduce defects caused by dried slurry on the backside of the wafer.

A backside defect and a frontside defect on a specimen may be correlated if a portion of the backside defect is opposite to a portion of the frontside defect. In particular, if a portion of a backside defect is aligned with a portion of a frontside defect along an axis perpendicular to the frontside and the backside of a specimen, the backside and frontside defects may be correlated. For example, turning now to the drawings, FIG. 1a illustrates a schematic view of a frontside of wafer 10 on which frontside defects 12 were detected. Although each frontside defect 12 illustrated in FIG. 1a is shown to have the same size and shape, it is to be understood that the frontside defects may have many different sizes and shapes. In addition, although four frontside defects are illustrated in FIG. 1a, it is to be understood that any number of such defects may be detected on the frontside of the wafer and in any location on the frontside of the wafer. Furthermore, it is noted that the dimensions illustrated in FIG. 1a (and all other figures described herein) are not drawn to scale. For example, the dimensions of frontside defects 12 in FIG. 1a are greatly exaggerated with respect to the dimensions of the wafer to illustrate spatial relationships between the frontside defects and backside defects on the specimen. Moreover, each of the figures are not drawn to the same scale.

As further illustrated in FIG. 1a, backside defects 14 were detected on a backside of the wafer. In this figure, the backside defects are illustrated as if the backside defects are being viewed from the frontside of the wafer through the thickness of the wafer. In this manner, the locations of the frontside and backside defects are illustrated as if the backside and frontside defects were detected on the same side of the specimen. As above, although some backside defects 14 illustrated in FIG. 1a are shown to have the same size and shape, it is to be understood that the backside defects may have many different sizes and shapes. In addition, although four backside defects are illustrated in FIG. 1a, it is to be understood that any number of such defects may be detected on the backside of the wafer and in any location on the backside of the wafer.

Figure 1B:
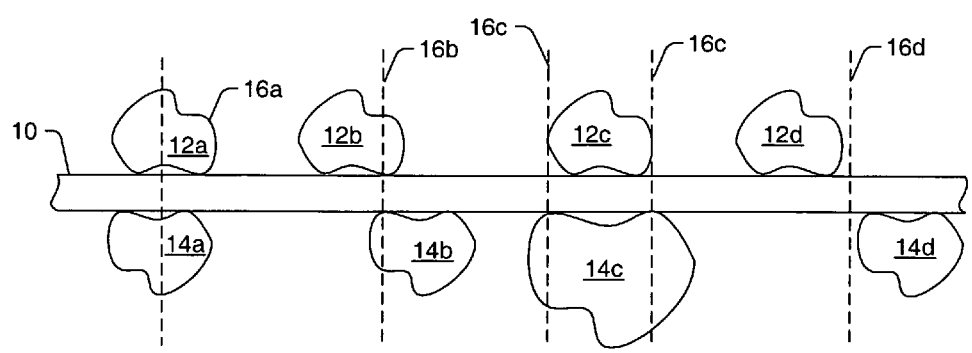
FIG. 1b is a cross-sectional view cross-sectional view along plane A of FIG. 1 illustrating the spatial orientation of frontside and backside defects that may and may not be correlated.

FIG. 1b is a cross-sectional view along plane A of FIG. 1 illustrating the spatial orientation of frontside and backside defects that may or may not be correlated. For example, a backside defect and a frontside defect on a specimen may be correlated only if a portion of the backside defect is opposite to a portion of the frontside defect, which may, in some instances, be determined by an area-to-area comparison. In other embodiments, the computer-implemented method may include comparing backside and frontside inspection data at each point, or set of coordinates, on the wafer in a point-to-point comparison and correlating points that are on opposite sides of the wafer and that both include defects. In a further embodiment, the computer-implemented method may include comparing backside or frontside inspection data at each point, or set of coordinates, on the wafer to an area of a defect on the other side of the wafer in a point-to-area comparison and correlating the point and the area if the point falls within the area. Although these embodiments are further described with respect to an area-to-area comparison, it is to be understood that this description of this method is not limited to area-to-area comparisons and equally applies to point-to-point comparisons and point-to-area comparisons.

The portion of the backside defect that is opposite to a portion of the frontside defect may include at least 5% of a cross-sectional area of the backside defect. The cross-sectional area may be defined in a direction parallel to the upper surface of the backside of the specimen. The portion of the backside defect may vary, however, depending upon, for example, the types of defects detected on the different sides of the specimen. For example, the portion of the backside defect may include at least 15%, at least 25%, at least 50%, at least 75%, or at least 100% of the cross-sectional area of the backside defect. Similarly, the portion of the frontside defect that is opposite to a portion of the backside defect may include at least 5% of a cross-sectional area of the frontside defect. This cross-sectional area may also be defined in a direction parallel to the upper surface of the frontside of the specimen. The portion of the frontside defect may vary, however, as described above. For example, the portion of the frontside defect may include at least 15%, at least 25%, at least 50%, at least 75%, or about 100% of the cross-sectional area of the frontside defect. A backside defect and a frontside defect that are correlated to each other may have different portions that are opposite to the other defect. For example, 100% of a frontside defect may be opposite to only 75%, 50%, 25%, 15%, or 5% of a backside defect.

One example of defects that may be correlated to each other include backside defect 14a and frontside defect 12a. As shown in FIG. 1b, almost 100% of backside defect 14a on the backside of specimen 12 is opposite to almost 100% of frontside defect 12a. In other words, almost all of backside defect 14a is aligned with almost all of frontside defect 12a along axis 16a, which is perpendicular to the frontside and the backside of specimen 10. However, since defects on both sides of the wafer tend to vary greatly in size and location, two defects may rarely have the similarities in size and location of backside defect 14a and frontside defect 12a. In a more common scenario, less than 100% of backside defect 14b is opposite to less than 100% of frontside defect 12b. However, backside defect 14b and frontside defect 12b may be correlated with one another in some cases because, as shown in FIG. 1b, at least a portion of backside defect 14b is aligned with at least a portion of frontside defect 12b along axis 16b, which is perpendicular to the frontside and the backside of specimen 10. Since backside defects may have larger dimensions than frontside defects in many cases, backside defect 14c and frontside defect 12c illustrate an even more common spatial relationship between two defects that may be correlated to one another. For example, as illustrated in FIG. 1b, 100% of frontside defect 12c is opposite to less than 100% of backside defect 14c. In addition, 100% of frontside defect 12c is aligned with less than 100% of backside defect 14c along any axis located between axes 16c, which are perpendicular to the frontside and the backside of the specimen. FIG. 1b also illustrates a frontside defect and a backside defect that will not be correlated to one another due to the different spatial locations of the defects on the specimen. For example, no portion of backside defect 14d is opposite to any portion of frontside defect 12d. In addition, no portion of backside defect 14d is aligned with any portion of frontside defect 12d along axis 16d. Therefore, these two defects would not be correlated to one another.

Figure 2:
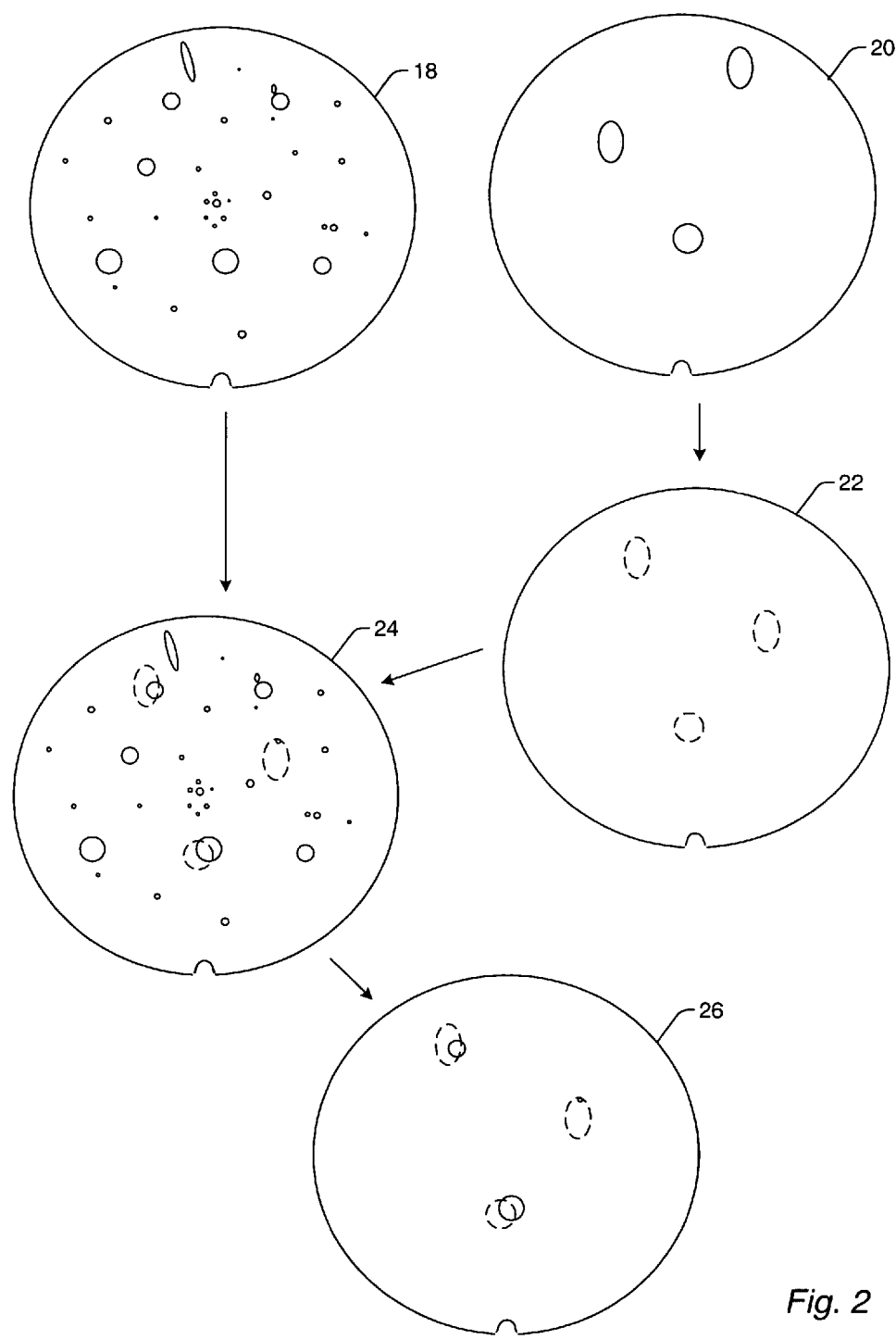
FIGS. 2 and 3 illustrates schematic diagrams of various visual representations of a specimen.

Generating a single visual representation of a specimen such as the illustration of FIG. 1a, which illustrates defects on both sides of a wafer as if they were detected on the same side of the wafer, may be generated in a number of ways. In one embodiment, the computer-implemented method may include generating visual representation 18 of the frontside of a specimen and generating visual representation 20 of the backside of the same specimen, as shown in FIG. 2. In some instances, the two visual representations may include images of the different sides of the specimen that were generated by one or more inspection systems. In one embodiment, the computer-implemented method may include receiving the images generated by the inspection system(s) in a format that is compatible with software used to carry out the method. Alternatively, the computer-implemented method may include receiving images or image data generated by the inspection system(s) and formatting the images or image data or performing a number of other functions on the image data such as, but not limited to, preprocessing the image data by altering the data to reduce the effects of distortion, alignment error, illumination non-uniformities, and/or detector non-uniformities, and preprocessing and culling of the images generated by the inspection system(s).

In other cases, the visual representation may include graphical representations, such as two-dimensional maps, of the different sides of the specimen. The two-dimensional maps may illustrate characteristics of the specimen as a function of position on the specimen. The characteristics may include, for example, color, topology of the specimen, roughness, and characteristics of structures formed on the specimen if the two-dimensional map is of the frontside of the specimen. In one embodiment, the computer-implemented method may include generating the two-dimensional maps using data generated by the inspection system(s) during inspection of the specimen. In addition, the computer-implemented method may include determining the characteristics of the specimen from the data generated by the inspection system(s). The two-dimensional maps may be generated using any method known in the art.

The computer-implemented method may also include altering one of the visual representations such that the altered visual representation appears as a mirror image of its original visual representation. For example, as shown in FIG. 2, visual representation 20 of the backside of the specimen may be altered to generate visual representation 22, which is a mirror image of visual representation 20. Altering a visual representation in this manner may be performed using any method known in the art. Altering one of the visual representations in this manner may reduce discrepancies between the visual representations of the specimen. For example, inspection systems may generate images of each side of the specimen by scanning the different sides of the specimen at different and opposite angles with respect to the surfaces of the specimen. In this manner, spatial positions of the defects in the images along one axis of a two-dimensional rectangular coordinate system that can be used to define the spatial positions will be opposite to each other. Therefore, altering one of the visual representations such that it is a mirror image of its original will allow a direct comparison of the visual representations of different sides of the specimen.

The computer-implemented method may also include superimposing the altered and the unaltered visual representations to generate an overall visual representation of the specimen. For example, as shown in FIG. 2, altered visual representation 22 of the backside of the specimen may be superimposed with unaltered visual representation 18 of the frontside of the specimen to generate overall visual representation 24 of the specimen. As shown in FIG. 2, overall visual representation 24 illustrates the backside defects and the frontside defects with different formatting (i.e., different line types) to visually differentiate the backside defects and the frontside defects. Other types of formatting, however, may be used to differentiate the backside and the frontside defect such as different colors.

The computer-implemented method may further include determining if a portion of a backside defect is opposite to a portion of a frontside defect from overall visual representation 24. For example, the computer-implemented method may simply determine if both types of defects are present at different locations in the overall visual representation. The computer-implemented method, however, may also be configured to determine if both types of defects are present at a location on the specimen using altered visual representation 22 and unaltered visual representation 18. Therefore, in some embodiments, overall visual representation 24 may not be generated. However, generating overall visual representation 24 may be an intermediate step to generating overall visual representation 26 illustrated in FIG. 2. As shown in FIG. 2, overall visual representation 26 does not illustrate backside defects and frontside defects that were not correlated to a frontside defect and a backside defect, respectively. For example, several of the frontside defects were not correlated to a backside defect and, therefore, are not illustrated in overall visual representation 26. However, each backside defect was correlated to at least one frontside defect and, therefore, each backside defect is illustrated in overall visual representation 26. In most instances, however, each backside defect will not be correlated to at least one frontside defect. Therefore, in many cases, overall visual representation 26 may also include fewer backside defects than overall visual representation 24 or visual representation 22. Overall visual representation 26 may be particularly useful to provide to a user. For example, because overall visual representation 26 is not cluttered with defects that could not be correlated, the overall visual representation may provide users with only the defect results that are of interest (i.e., backside defects that may have contributed to frontside defects).

In another embodiment, the computer-implemented method may include correlating backside defects and frontside defects during processing of the defect data. For example, the computer-implemented method may include comparing coordinates defining a location of a backside defect with coordinates defining a location of a frontside defect to determine if a portion of the backside defect is opposite to a portion of the frontside defect. In some embodiments, the method may also include altering the coordinates defining the location of the backside defect or altering the coordinates defining the location of the frontside defect prior to comparing the coordinates. In this manner, the locations of the backside defects and the frontside defects may be defined as if the backside and frontside defects were determined on the same side of the specimen. In yet another embodiment, the computer-implemented method may include comparing backside and frontside inspection data at each point, or set of coordinates, on the wafer after the coordinates have been altered as described herein.

As described above, for example, an inspection system will inspect a specimen from different sides of the specimen thereby resulting in images or image data of the different sides that have different, and in some instances opposite, coordinates along one axis of a two-dimensional rectangular coordinate system used to define spatial positions on the specimen. The images or image data of the different sides may also have coordinates that are different, or offset, from each other along both axes of the two-dimensional rectangular coordinate system. These differences may be caused by differences in alignment of a specimen prior to each inspection or if a coordinate system used to define locations on an unpatterned surface of the specimen is different than a coordinate system used to define locations on a patterned surface of a specimen. Therefore, the coordinates of one of the images or one set of image data may be altered to standardize the coordinates of both images or sets of image data. In some embodiments, the coordinates or both images of both sets of image data may be altered to standardize the coordinates. In either case, the method may determine if a defect is present on opposing sides of a specimen at the same position on a specimen as defined by the standardized coordinates.

In some embodiments, although one image or set of image data may be offset from the other image or image data, the coordinates of both images or sets of image data may be reported in a data output format using a common coordinate system such as KLARF, which is a standard data output format on many inspection systems commercially available from KLA-Tencor. In such embodiments, software such as the KLARF KoProcessor, which is also commercially available from KLA-Tencor, may be used to alter the coordinates as described above. The KLARF KoProcessor is a stand-alone utility that monitors a given input directory for the presence of a KLARF file, reads the KLARF file to determine if the data is collected from a backside scan, and if so, alters, "mirrors," or translates the coordinates as described above. In this manner, backside defects may be reported as if viewed from the frontside of the wafer. The resulting file may then be used to correlate backside defects and frontside defects as described above.

Additionally, inspection systems available from KLA-Tencor may also include software that can automatically "mirror" the backside defect coordinates. Once example of such a system is the SP1 laser-based wafer inspection tool. The software may be executed when defect "mirroring" is selected by a user. Alternatively, the software may be executed if indicated in instructions of a recipe for an inspection process being carried out on the system.

In additional embodiments, the computer-implemented method may include identifying data that is representative of a signature of a chuck, or a wafer handler, of a process tool within data generated during inspection of the backside of the specimen. The signature of a chuck, or a wafer handler, may also be commonly referred to as a "fingerprint" of the chuck or the wafer handler. For example, the chuck or the wafer handler contacts the backside of the specimen while the specimen is processed in the process tool. Some chucks or wafer handlers may alter the backside of the specimen in a repeatable manner. For example, a chuck may leave material on the backside of the specimen in predictable locations. In another example, a wafer handler may scratch the backside of the specimen in a repeatable fashion. Different chucks and different wafer handlers often have different signatures. Therefore, a signature for more than one or each chuck and wafer handler in a process tool or several process tools may be determined such that regardless of what steps have been performed on the specimen prior to inspection, the correct signature of the chuck or wafer handler may be identified in the inspection data. The signature of the chuck may be determined prior to processing of the wafer. For example, during qualification of a process tool, several wafers or lots of wafers may be processed in the process tool, and an average signature of the chuck may be determined by inspecting each wafer. Therefore, the signature of the chuck or the wafer handler may define a baseline representation of the manner in which a chuck or wafer handler may alter the backside of a specimen without causing yield loss.

Such embodiments may, therefore, include removing the data representing the signature of the chuck or the wafer handler from the inspection data of the backside of the specimen prior to correlating the defects. This step may also be commonly referred to as "paddle image removal," "puck image removal," and "end effector image removal." In this manner, the data representing the signature of the chuck or the wafer handler may be separated from data representing potential, or actual, defects on the backside of the specimen. In addition, the data representing the signature of the chuck may not be considered during correlation of frontside defects and backside defects. As such, data generated during detection of the frontside defects may not be erroneously correlated with the data representing the signature of the chuck.

When dealing with micro defects for which an inspection system cannot assign meaningful lateral dimensions, many inspection systems report such defects as mathematical points ("point defects"). Any systematic and/or random errors in the x and/or y coordinates of the mathematical points might cause a correlation algorithm or method to decide that a point defect does not correlate with a defect on the opposite side of a specimen because they do not perfectly coincide (in the case of frontside and backside point defects) or because the point defect's perpendicular projection does not intercept the other defect's outline.

Figure 3:
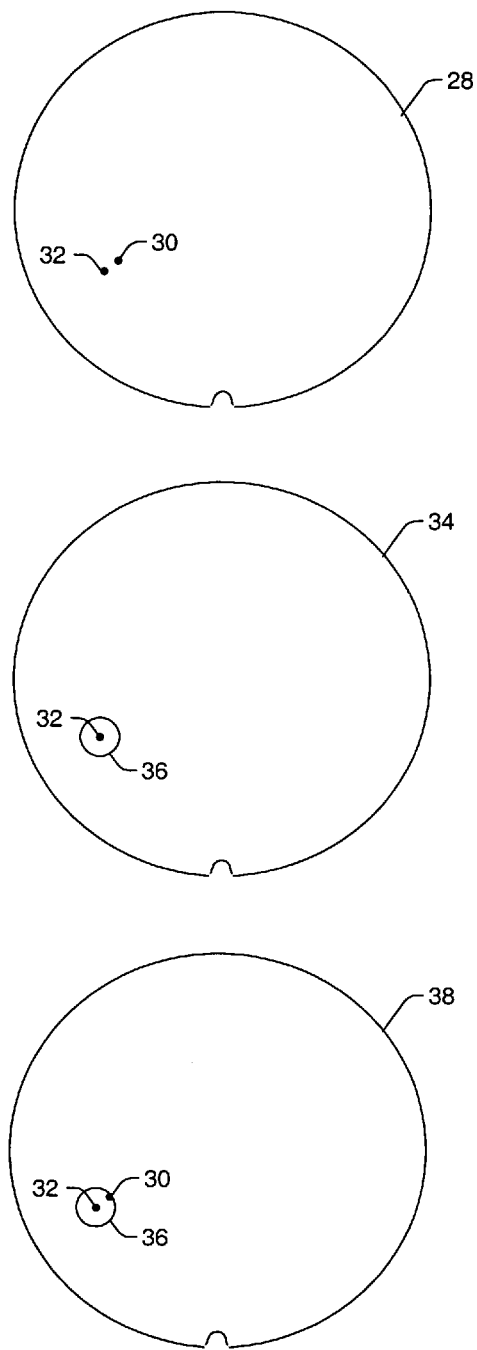

For example, as shown in FIG. 3, visual representation 28 shows two point defects 30 and 32. Point defect 30 is a frontside'defect. Point defect 32 is a backside defect. The coordinates of the backside defect have been translated as described above, and visual representation 28 may be generated as described above by superimposing the altered representation of the backside of the specimen and the unaltered representation of the frontside of the specimen. The dimensions of the point defects shown in FIG. 3 are greatly exaggerated with respect to the dimensions of the specimen for clarity. As can be seen in FIG. 3, although point defects 30 and 32 are relatively close to each other indicating potential causality, the point defects do not perfectly coincide and do not overlap at all. As such, a correlation algorithm or method may determine that point defects 30 and 32 are not correlated.

Thus, a strict "must intercept" correlation rule for point-to-point and point-to-area comparisons may lead to an unacceptable rate of missed correlations. A method to decrease this false negative rate is to "inflate" the point defect into a geometrical figure with lateral dimensions (such as a circle with radius r centered on the point defect). For example, as shown in FIG. 3, visual representation 34 shows geometrical FIG. 36, which is a circle with radius r centered on point defect 32. If the geometrical figure overlaps a defect, a point defect, or another geometrical figure on the opposite side, according to the percentage of common area rule and/or other rules described herein, then the defects may be considered to be correlated. For example, as shown in visual representation 38, even though point defect 30 is not opposite to point defect 32, the defects may be correlated since geometrical FIG. 36 at least partially overlaps point defect 30 on the opposite side of the specimen.

The degree of point defect inflation may be determined based on the tradeoff between decreasing false negatives vs. increasing false positives (e.g., deciding that a defect is correlated to another defect on the opposite side when in fact there is not causal connection between them).

Accordingly, to reduce the problems associated with point defects described above, a computer-implemented method includes correlating a backside defect detected on a backside of a specimen with a frontside defect detected on a frontside of the specimen if the backside defect and the frontside defect satisfy one or more proximity criteria. In one embodiment, the method may also include defining the backside defect as a geometrical figure having lateral dimensions larger than the backside defect. The geometrical figure may be an inflated point, which surrounds a point defect. Inflated points, often defined by a "search radius," are used in classification and spatial signature algorithms based on the concept of nearest-neighbor searches. U.S. Pat. No. 5,991,699 to Kulkarni et al., which is incorporated by reference as if fully set forth herein, describes using inflated points for identifying groups of defects that may have the same causation. However, the inflated points and clustering techniques described by Kulkarni have not been used to relate defects on the opposite sides of a wafer.

In such an embodiment, the one or more proximity criteria may be satisfied if at least a portion of the geometrical figure is opposite to at least a portion of the frontside defect, as shown in visual representation 38 of FIG. 3. In addition or alternatively, the method may include defining the frontside defect as a geometrical figured having lateral dimensions larger than the frontside defect. Therefore, frontside and/or backside defects may be "inflated" and correlated with defects on the opposite side of the specimen. In such embodiments, the one or more proximity criteria may be satisfied if at least a portion of the geometrical figure is opposite to at least a portion of the backside defect or at least a portion of a geometrical figure defining the backside defect. In some embodiments, the one or more proximity criteria may be satisfied if at least a portion of the backside defect is opposite to at least a portion of the frontside defect. Such proximity criteria may be particularly suitable non-point defects.

In another embodiment, the computer-implemented methods described herein may include classifying one or more backside defects detected on a specimen. In one embodiment, classification of the backside defects may include analyzing data representing spatial characteristics of the backside defects. For example, analyzing the data may include spatial signature analysis of data generated by inspection of the backside of the specimen. Spatial signature analysis (SSA) is an automated whole-wafer analysis technique that can intelligently group, or cluster, wafermap defects together into spatial signatures that can be uniquely assigned to specific manufacturing processes and tools. SSA can be used to rapidly resolve systematic problems by assigning a label to a unique distribution, or a "signature," of defects based on historical data about different processes and equipment. SSA generally includes applying proximity clustering to unrelated clusters of defects and performing data reduction by clustering defects together into extended spatial groups and assigning a classification to the group that indicates a possible source such as a scratch, a particle, or other contamination. SSA is known in the art, and further description of SSA can be found in the "Handbook of Silicon Semiconductor Metrology" edited by Alain C. Diebold, Marcel Dekker, Inc., New York, 2001, pp. 694-698, which is incorporated by reference as if fully set forth herein.

The computer-implemented method, however, may include classifying the backside defects, and usually the frontside defects, using any other technique known in the art. For example, the Sobel operator technique, which is known in the art, may be used to find defects of a specific shape in a defect image. Using the Sobel operator, a vertical rectangle may be distinguished from a horizontal rectangle of approximately the same size and shape. In another example, classifying the defects may include grouping defects based on features of the defects extracted from the images. Examples of methods that may be used for grouping of defects include, but are not limited to, the Kohonen mapping technique, a K-means, and a method described by N. Otsu in "A Threshold Selection Method from Gray-Level Histograms," IEEE Trans. Systems, Man, and Cybernetics, Vol. SMC-9, 1979, pp. 62-66. In addition, classifying the defects may include grouping the defects using invariant core classes as illustrated in PCT Publication No. WO 00/03234 to Ben-Porath et al., which is incorporated by reference as if fully set forth herein. One or more of the extracted features may also be weighted, and the extracted features may be compared accordingly as illustrated in PCT Publication No. WO 01/40145 to Baker et al., which is incorporated by reference as if fully set forth herein. Furthermore, the extracted features of defects may be compared to features of classified defects in a database such as a knowledge database as illustrated in U.S. Pat. No. 6,104,835 to Han, which is incorporated by reference as if fully set forth herein. In an additional embodiment, classifying defects may include applying a number of filtering algorithms in series as illustrated in U.S. Pat. No. 6,233,719 to Hardikar et al. and PCT Publication No. WO 99/22310 to Hardikar et al., which are incorporated by reference as if fully set forth herein.

In some embodiments, the method may include determining parameters for classification of a frontside defect based on the classification of a backside defect correlated to the frontside defect. For example, the number of possible classes that may be considered for the frontside defect may be reduced based on the classification of the backside defect. For instance, as described above, if the backside defect is a particle, then a scratch may not be considered as a possible classification for a frontside defect correlated to this particle. Determining parameters for classification of the frontside defect may increase the accuracy of such classification and may increase the throughput of the defect analysis or review process.

The results generated by classifying the backside and/or frontside defects may be displayed in a number of ways. For example, the results may be displayed such that backside and/or frontside defects having different classifications may be distinguished from each other. In such a display, backside and/or frontside defects having different classifications may be indicated by different colors, flags, or other designations. The results may also be displayed in a bar chart or a two-dimensional map and the different classifications may be indicated by different colors, shading, background, flags, or any other such designation. The results of defect classification may also be output to a number of modules such as a display medium, a printer, a storage medium, a database, and a fab database. A fab database may include information related to any of the processes performed in a fab such as tool history, wafer history, and reticle history. A fab database may also include any set of data suitable for use in an overall fab management system. An example of such a system is illustrated in PCT Publication No. WO 99/59200 to Lamey et al., which is incorporated by reference as if fully set forth herein. For example, the computer-implemented method may include accessing a fab database and sending information to the fab database.

In some embodiments, the computer-implemented method may include determining a root cause of the backside defects. Example's of root causes include, but are not limited to, chemical smears, grain, haze, microscoring, wand marks, brush marks, rail marks, impact marks, hot spots, shower patterns, exposure shutter patterns, doughnut patterns, poorly or unevenly developed layers on the reticle, over etching, under etching, and thermal variation. The computer-implemented method may include using features of the defect to determine a root cause of the defect. Defects that have approximately the same features are likely to have the same cause. Determining a root cause of the defects may, therefore, include grouping the defects using various features of the defects described above to cluster defects that may have the same causation. Clustering as a technique for identifying groups of defects that may have the same causation is illustrated in U.S. Pat. No. 5,991,699 to Kulkarni et al., which is incorporated by reference as if fully set forth herein.

In addition, the root cause of backside defects may also be determined from data representing processing history of the specimen. Such data may represent parameters of processing of the specimen such as, but not limited to, time, temperature, tool, and tool history. In other embodiments, the root cause of backside defects may be determined from data representing processing history and backside defects on other specimen. For example, similar backside defects on multiple wafers processed in the same tool may indicate which tool is causing the backside defects. Additional analysis of the tool may indicate what parameter of the tool is causing the backside defects. In one example, pitting defects on the backside of wafers may be determined to be caused by contamination that was present on the chuck of an etch tool prior to etching of the wafers. The contamination may have marginalized contact between the chuck and the wafer during etch, which may have, in turn, caused the pitting defects on the backside of the wafers. Such information may be obtained from a fab database or from a processor coupled directly to a process tool. In this manner, the computer-implemented method may include obtaining information from process tools related to processing of the specimen in these tools. In addition, the method may include using software such as Klarity ACE root-cause analysis software available from KLA-Tencor to determine a root cause of the backside defects. The results of root cause determination may also be output to a number of modules as described herein.

In some cases, the root cause of backside defects may be analyzed in more detail by experimental methods. For example, chemical analysis methods such as Vapor Phase Decomposition Inductively Coupled Plasma Mass Spectrometry (VPD-ICP) and Total Reflection X-Ray Fluorescence spectrometry (TXRF) may be used to examine wafer level contamination such as metallic contamination. A scanning electron microscopy (SEM) review tool may also be used to determine defect type, size, and composition. In addition, as an alternative to wafer-level analysis, the composition of defects may be determined using energy dispersive X-ray spectography (EDX). This analysis may be particularly useful for examining frontside defects on product and non-product wafers and backside defects on non-product wafers. This analysis may also be used to examine backside defects on product wafers if non-destructive, edge handling SEM tools configured to perform EDX become commercially available.

The computer-implemented method may also include determining a root cause of a frontside defect. In one embodiment, the computer-implemented method may also include determining a root cause of frontside defects from a determined classification or root cause of backside defects correlated to the frontside defects. For example, if a backside defect is classified as a particle, a frontside defect correlated to this backside defect may be classified as an out-of-focus defect having the particle as a root cause. In this manner, if backside defects can be identified as a root cause of frontside defects based on classification of the backside defects, the possibility that another parameter of a process caused the frontside defect may be ruled out. Therefore, correlating backside defects and frontside defects at common locations on a specimen may provide substantially accurate determinations of the root causes of the frontside defects and substantially accurate corrections of the root causes.

In additional embodiments, the method may include altering a parameter of a process tool in response to the classification of the backside defect. Preferably, the method may include altering a parameter of a process tool in response to a backside defect that was correlated to a frontside defect to reduce occurrence of the frontside defect and/or the backside defect on additional specimen processed in the process tool. For example, if a backside defect such as dried CMP slurry on the backside of a specimen is shown to correlate to, or cause, frontside defects on the frontside of the specimen, the method may include altering a post-CMP rinse or cleaning step to remove more of the slurry from the backside of the specimen, particularly, before the slurry can dry onto the specimen. In another example, if residual resist on a backside of a specimen is shown to correlate to, or cause, frontside defects resulting from micro-arcing in an etch process, the method may include altering a coating or develop step of a lithography process to remove such residual resist from additional specimen processed in the same lithography process. In a further example, as described above, pitting defects on the backside of wafers may be caused by contamination on a chuck in an etch tool. Such pitting defects may cause out-of-focus defects on the frontside of a wafer after lithography. Therefore, altering a parameter of the etch process may include cleaning or replacing the chuck in the etch tool.

In yet another example, if particles on the backside of a specimen are shown to cause exposure tool aborts during lithography, then the method may include altering a parameter of the process performed prior to lithography such as oxide deposition or adding a cleaning step prior to lithography. In this example, the parameter of the oxide deposition which is altered may include a parameter of a chuck or a wafer handler used for the oxide deposition or a parameter related to seasoning of the deposition chamber. In one particular example, the chuck used for oxide deposition may be cleaned to remove particles or other contamination from the chuck that may have been causing void formation between the wafer and the heater pedestal during deposition, which in turn may cause micro-arcing. Furthermore, the method may include monitoring backside defects over time and determining when process tools should be cleaned or maintained. Moreover, reducing the occurrence of backside defects may reduce damage that such defects may cause to process tools. For example, residual resist on the backside of wafers may cause the wafers to adhere to a chuck or wafer handler of another process tool, which could significantly damage the process tool thereby resulting in process tool downtime and high costs associated with maintenance and repair of the process tool. In yet another example, the computer-implemented methods described herein may be particularly useful for detecting wafer handlers that are out of control (i.e., or causing damage to or breakage of wafers) in a fully-automated fab since this type of problem may not be detected by an operator working at the tool. In this manner, detecting a backside defect, correlating the backside defect to a frontside defect, classifying the backside defect, and altering a parameter of a process tool in response to the classification of the backside defect can significantly improve the yield of semiconductor manufacturing processes.

In addition, since some backside defects may not be correlated with frontside defects, it may be reasonable to assume that such backside defects may not contribute, or may not contribute significantly, to yield loss. As such, the computer-implemented methods described above may also be used to identify backside defects for which process corrections should be made to reduce occurrence of the backside defects. In this manner, the computer-implemented method may be used to identify yield-reducing backside defects and non-yield-reducing backside defects, which may also be referred to as "nuisance" backside defects. Being able to categorize backside defects in such a manner may reduce the complexity and difficulty of accurately altering parameters of processes and tools because, in some cases, corrections may only need to be made for a portion of the backside defects. However, even backside defects that are correlated to frontside defects may not contribute to reduction in yield if the frontside defects do not contribute to yield. Therefore, the method may further include correlating the backside defects to electrical test results of the wafer at the position of the backside defects. Since the backside defects have been correlated to the frontside defects, determining which electrical test results correlate to the backside defects is relatively trivial. In this manner, backside defects that ultimately reduce semiconductor fabrication processing yield may be easily and accurately determined.

In some instances classification of the backside or frontside defects may also be used to determine parameters for repair of the backside or frontside defects, respectively. Examples of systems and methods that may be used to repair backside or frontside defects are illustrated in United States Patent Application entitled: "Methods and Systems for Closed Loop Defect Reduction" by Marella, which is incorporated by reference as if fully set forth herein.

Program instructions implementing methods or one or more steps of the methods such as those described above may be transmitted over or stored on a carrier medium. The carrier medium may be a transmission medium such as a wire, cable, or wireless transmission link, or a signal traveling along such a wire, cable, or link. The carrier medium may also be a storage medium such as a read-only memory, a random access memory, a magnetic or optical disk, or a magnetic tape. One or more data structures and/or rules databases may similarly be transmitted over or stored upon such a carrier medium.

Each of the computer-implemented methods described herein may be performed substantially automatically by a system configured to execute the program instructions. Alternatively, one or more steps of the computer-implemented methods may be designed to be performed either automatically or with some operator intervention. For example, one or more of the steps of the methods may include receiving parameters for classification of the defects from an operator or allowing the operator to select which steps of the methods are carried out for a particular specimen. Therefore, the system may be configured with some flexibility such that the computer-implemented methods may be carried out in a number of ways.

According to another embodiment, a computer system may be configured to operate software to perform at least one step of the computer-implemented methods described above. The computer system may include a memory medium on which computer programs may be stored for carrying out the computer-implemented methods. The term "memory medium" is intended to include an installation medium, e.g., a CD-ROM, or floppy disks, a computer system memory such as DRAM, SRAM, EDO RAM, Rambus RAM, etc., or a non-volatile memory such as a magnetic media, e.g., a hard drive, or optical storage. The memory medium may include other types of memory as well, or combinations thereof. In addition, the memory medium may be located in a first computer in which the programs are executed, or may be located in a second different computer that connects to the first computer over a network. In the latter instance, the second computer provides the program instructions to the first computer for execution. Also, the computer system may take various forms, including a personal computer system, mainframe computer system, workstation, network appliance, Internet appliance, personal digital assistant ("PDA"), television system or other device. In general, the term "computer system" may be broadly defined to encompass any device having a processor, which executes instructions from a memory medium.

In some instances, in which the computer-implemented methods involve manipulating or using images or image data, the computer system may include a processor configured for processing of such images or image data. Examples of appropriate processors include, but are not limited to, a Silicon Graphics 0-200 computer available from Silicon Graphics, Mountain View, Calif., an HP735 workstation available from Hewlett Packard, Palo Alto, Calif., and a Sun SPARC or Sun ULTRASPARC system available from Sun Microsystems, Sunnyvale, Calif.

The memory medium may be configured to store a software program for the operation of the system to perform at least one step of the computer-implemented methods described above. The software program may be implemented in any of various ways, including procedure-based techniques, component-based techniques, and/or object-oriented techniques, among others. For example, the software program may be implemented using ActiveX controls, C++ objects, JavaBeans, Microsoft Foundation Classes ("MFC"), or other technologies or methodologies, as desired. A CPU, such as the host CPU, executing code and data from the memory medium may include a means for creating and executing the software program according to the methods described above.

Further modifications and alternative embodiments of various aspects of the invention may be apparent to those skilled in the art in view of this description. For example, computer-implemented methods for correlating backside and frontside defects detected on a specimen and computer-implemented methods for classifying backside defects are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A computer-implemented method, comprising:
    determining if a portion of a backside defect detected on a backside of a specimen is opposite to a portion of a frontside defect detected on a frontside of the specimen;
    correlating the backside defect with the frontside defect if the portion of the backside defect is determined to be opposite to the portion of the frontside defect; and
    generating a single visual representation of the specimen that illustrates the backside defect and the frontside defect with different formatting to visually differentiate the backside defect and the front side defect.

2. The method of claim 1, wherein the portion of the backside defect is aligned with the portion of the frontside defect along an axis perpendicular to the frontside and the backside of the specimen.

3. The method of claim 1, further comprising identifying data representative of a signature of a chuck of a process tool within data generated during detection of the backside defect and removing the data representative of the signature of the chuck from the data generated during detection of the backside defect prior to said correlating.

4. The method of claim 1, further comprising generating visual representations of the frontside and the backside of the specimen, altering one of the visual representations such that the altered visual representation appears as a mirror image of the one visual representation, and superimposing the altered and the unaltered visual representations to generate an overall visual representation of the specimen.

5. The method of claim 4, wherein said determining comprises determining if the portion of the backside defect on the backside of the specimen is opposite to the portion of the frontside defect on the frontside of the specimen from the overall visual representation.

6. The method of claim 4, wherein the overall visual representation does not illustrate additional backside defects detected on the specimen and additional frontside defects detected on the specimen, and wherein the additional backside defects are not correlated with the additional frontside defects.

7. The method of claim 1, wherein said determining comprises comparing coordinates defining a location of the backside defect with coordinates defining a location of the frontside defect to determine if the portion of the backside defect on the backside of the specimen is opposite to the portion of the frontside defect on the frontside of the specimen.

8. The method of claim 7, further comprising altering the coordinates defining the location of the backside defect or the coordinates defining the location of the frontside defect prior to said comparing such that the locations of the backside defect and the frontside defect are defined as if the frontside and backside defects were detected on the same side of the specimen.

9. The method of claim 1, further comprising classifying the backside defect.

10. The method of claim 1, further comprising classifying the backside defect and determining a root cause of the backside defect from data representing processing history of the specimen.

11. The method of claim 1, further comprising classifying the backside defect and determining parameters for classifying the frontside defect from the classification of the backside defect.

12. The method of claim 1, further comprising classifying the backside defect and determining a root cause of the frontside defect from the classification of the backside defect.

13. The method of claim 1, further comprising classifying the backside defect and altering a parameter of a process tool in response to the classification.

14. The method of claim 1, further comprising altering a parameter of a process tool in response to the backside defect to reduce occurrence of the frontside defect on additional specimen processed in the process tool.

15. A computer-implemented method, comprising:
    defining a backside defect detected on a backside of a specimen as a geometrical figure having lateral dimensions larger than the backside defect;
    determining if the backside defect and a frontside defect detected on a frontside of the specimen satisfy one or more proximity criteria, wherein the one or more proximity criteria are satisfied if at least a portion of the geometrical figure is opposite to at least a portion of the frontside defect; and
    correlating the backside defect with the frontside defect if the backside defect and the frontside defect satisfy the one or more proximity criteria.

16. The method of claim 15, further comprising defining the frontside defect as a geometrical figure having lateral dimensions larger than the frontside defect, wherein the one or more proximity criteria are satisfied if at least a portion of the geometrical figure is opposite to at least a portion of the backside defect.

17. The method of claim 15, wherein the one or more proximity criteria are satisfied if at least a portion of the backside defect is opposite to at least a portion of the frontside defect.

18. A computer-implemented method, comprising:
    analyzing data representing spatial characteristics of backside defects detected on a specimen to classify the backside defects;

determining if data generated during detection of the backside defects is representative of a signature of a chuck of a process tool;
removing the data representative of the chuck from data generated during detection of the backside defects;
determining if a portion of one of the backside defects detected on a backside of the specimen is opposite to a portion of a frontside defect detected on a frontside of the specimen; and
correlating the one of the backside defects with the frontside defect if the portion of the one of the backside defects is determined to be opposite to the portion of the frontside defect.

19. The method of claim 18, wherein said analyzing comprises spatial signature analysis of the data.

* * * * *